(12) United States Patent
Dimmer et al.

(10) Patent No.: US 7,778,687 B2
(45) Date of Patent: *Aug. 17, 2010

(54) IMPLANTABLE MARKER WITH A LEADLESS SIGNAL TRANSMITTER COMPATIBLE FOR USE IN MAGNETIC RESONANCE DEVICES

(75) Inventors: Steven C. Dimmer, Bellevue, WA (US); Eric Hadford, Snohomish, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 699 days.

This patent is subject to a terminal disclaimer.

(21) Appl. No.: 10/745,097

(22) Filed: Dec. 23, 2003

(65) Prior Publication Data

US 2004/0138554 A1   Jul. 15, 2004

Related U.S. Application Data

(63) Continuation of application No. 10/334,698, filed on Dec. 30, 2002, now Pat. No. 7,289,839.

(51) Int. Cl.
*A61B 5/05* (2006.01)
*A61B 19/00* (2006.01)

(52) U.S. Cl. .................................. 600/424; 128/899
(58) Field of Classification Search ................. 600/419, 600/423; 128/899; 340/572.5
See application file for complete search history.

(56) References Cited

U.S. PATENT DOCUMENTS 3,752,960 A    8/1973   Walton 3,836,842 A    9/1974   Zimmermann et al.

(Continued)

FOREIGN PATENT DOCUMENTS

EP    0719420    7/1996

(Continued)

OTHER PUBLICATIONS

International Search Report dated May 24, 2005, PCT Application No. PCT/US03/41329—related to the present application.

(Continued)

*Primary Examiner*—Eric F Winakur
*Assistant Examiner*—Michael T Rozanski
(74) *Attorney, Agent, or Firm*—Perkins Coie LLP (57) ABSTRACT

A leadless marker for localizing the position of a target within a patient. In one embodiment, the marker includes a casing, a resonating circuit, and a ferromagnetic element. The casing is configured to be positioned at a selected location relative to a target site in the patient; the casing, for example, can be configured to be permanently or semi-permanently implanted into the patient. The resonating circuit has an inductor within the casing comprising a plurality of windings of a conductor, but it does not have external electrical lead lines extending through the casing. The ferromagnetic element is at least partially within the inductor. The ferromagnetic element has a volume such that when the marker is in an imaging magnetic field having a field strength of 1.5 T and a gradient of 3 T/m, then the force exerted on the marker by the imaging magnetic field is not greater than gravitational force exerted on the marker.

29 Claims, 3 Drawing Sheets

U.S. PATENT DOCUMENTS

| | | |
|---|---|---|
| 3,967,161 A | 6/1976 | Lichtblau |
| 4,017,858 A | 4/1977 | Kuipers |
| 4,023,167 A | 5/1977 | Wahlstrom |
| 4,065,753 A | 12/1977 | Paul, Jr. |
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson |
| 4,230,123 A | 10/1980 | Hawkins |
| 4,260,990 A | 4/1981 | Lichtblau |
| 4,393,872 A | 7/1983 | Reznik |
| 4,395,910 A | 8/1983 | Thomenius |
| 4,466,075 A | 8/1984 | Groch |
| 4,618,978 A | 10/1986 | Cosman |
| 4,633,250 A | 12/1986 | Anderson |
| 4,642,786 A | 2/1987 | Hansen |
| 4,643,196 A | 2/1987 | Tanaka |
| 4,737,794 A | 4/1988 | Jones |
| 4,795,995 A | 1/1989 | Eccleston |
| 4,799,495 A | 1/1989 | Hawkins |
| 4,832,055 A | 5/1989 | Palestrant |
| 4,849,692 A | 7/1989 | Blood |
| 4,909,789 A | 3/1990 | Taguchi |
| 4,936,823 A | 6/1990 | Colvin |
| 4,945,305 A | 7/1990 | Blood |
| 4,992,794 A | 2/1991 | Brouwers |
| 4,994,079 A | 2/1991 | Genese |
| 5,031,634 A | 7/1991 | Simon |
| 5,050,608 A | 9/1991 | Watanabe |
| 5,062,847 A | 11/1991 | Barnes |
| 5,095,224 A | 3/1992 | Renger |
| 5,099,845 A | 3/1992 | Besz |
| 5,107,862 A | 4/1992 | Fabian |
| 5,142,292 A | 8/1992 | Chang |
| 5,170,055 A | 12/1992 | Carroll |
| 5,188,368 A | 2/1993 | Ryan |
| 5,197,466 A | 3/1993 | Marchosky |
| 5,198,877 A | 3/1993 | Schulz |
| 5,205,289 A | 4/1993 | Hardy |
| 5,211,129 A | 5/1993 | Taylor |
| 5,211,164 A | 5/1993 | Allen |
| 5,221,269 A | 6/1993 | Miller |
| 5,223,851 A | 6/1993 | Hadden |
| 5,230,338 A | 7/1993 | Allen |
| 5,240,011 A | 8/1993 | Assa |
| 5,246,005 A | 9/1993 | Carroll |
| 5,262,772 A | 11/1993 | Urbas |
| 5,325,873 A | 7/1994 | Hirschi |
| 5,377,678 A | 1/1995 | Dumoulin |
| 5,397,329 A | 3/1995 | Allen |
| 5,411,026 A | 5/1995 | Carol |
| 5,417,210 A | 5/1995 | Funda |
| 5,425,367 A | 6/1995 | Shapiro |
| 5,425,382 A | 6/1995 | Golden |
| 5,446,548 A | 8/1995 | Gerig |
| 5,453,686 A | 9/1995 | Anderson |
| 5,509,900 A | 4/1996 | Kirkman |
| 5,515,853 A | 5/1996 | Smith |
| 5,526,812 A | 6/1996 | Dumoulin |
| 5,528,651 A | 6/1996 | Leksell |
| 5,546,951 A | 8/1996 | Ben-Haim |
| 5,558,091 A | 9/1996 | Acker |
| 5,568,809 A | 10/1996 | Ben-Haim |
| 5,572,999 A | 11/1996 | Funda |
| 5,617,857 A | 4/1997 | Chader |
| 5,622,170 A | 4/1997 | Schulz |
| 5,622,187 A | 4/1997 | Carol |
| 5,629,967 A | 5/1997 | Leksell |
| 5,630,431 A | 5/1997 | Taylor |
| 5,645,065 A | 7/1997 | Shapiro |
| 5,680,106 A | 10/1997 | Schrott |
| 5,681,326 A | 10/1997 | Lax |
| 5,697,384 A | 12/1997 | Miyawaki |
| 5,707,362 A | 1/1998 | Yoon |
| 5,707,390 A | 1/1998 | Bonutti |
| 5,727,552 A | 3/1998 | Ryan |
| 5,745,545 A | 4/1998 | Hughes |
| RE35,816 E | 6/1998 | Schulz |
| 5,764,052 A | 6/1998 | Renger |
| 5,769,861 A | 6/1998 | Vilsmeier |
| 5,779,638 A | 7/1998 | Vesely |
| 5,782,775 A | 7/1998 | Milliman |
| 5,797,849 A | 8/1998 | Vesely |
| 5,805,661 A | 9/1998 | Leksell |
| 5,815,076 A | 9/1998 | Herring |
| 5,817,022 A | 10/1998 | Vesely |
| 5,817,092 A | 10/1998 | Behl |
| 5,820,553 A | 10/1998 | Hughes |
| 5,823,192 A | 10/1998 | Kalend |
| 5,828,770 A | 10/1998 | Leis |
| 5,830,144 A | 11/1998 | Vesely |
| 5,840,148 A | 11/1998 | Campbell |
| 5,868,673 A | 2/1999 | Vesely |
| 5,868,675 A | 2/1999 | Henrion |
| 5,879,297 A | 3/1999 | Haynor |
| 5,879,357 A | 3/1999 | Heaton |
| 5,895,235 A | 4/1999 | Droz |
| 5,902,238 A | 5/1999 | Golden |
| 5,902,310 A | 5/1999 | Foerster |
| 5,907,395 A | 5/1999 | Schulz |
| 5,910,144 A | 6/1999 | Hayashi |
| 5,913,820 A | 6/1999 | Bladen |
| 5,923,417 A | 7/1999 | Leis |
| 5,951,481 A | 9/1999 | Evans |
| 5,963,132 A | 10/1999 | Yoakum |
| 5,987,349 A | 11/1999 | Schulz |
| 5,989,265 A | 11/1999 | Bouquet De La Joliniere et al. |
| 6,015,390 A | 1/2000 | Krag |
| 6,019,725 A | 2/2000 | Vesely |
| 6,026,818 A | 2/2000 | Blair |
| 6,049,587 A | 4/2000 | Leksell |
| 6,052,477 A | 4/2000 | Wang |
| 6,059,734 A | 5/2000 | Yoon |
| 6,061,644 A | 5/2000 | Leis |
| 6,064,904 A | 5/2000 | Yanof |
| 6,067,465 A | 5/2000 | Foo |
| 6,076,008 A | 6/2000 | Bucholz |
| 6,082,366 A | 7/2000 | Andra |
| 6,094,007 A | 7/2000 | Faul |
| 6,097,007 A | 8/2000 | Wang |
| 6,097,994 A | 8/2000 | Navab |
| 6,129,658 A | 10/2000 | Delfino |
| 6,130,612 A | 10/2000 | Castellano |
| 6,140,740 A | 10/2000 | Porat |
| 6,144,875 A | 11/2000 | Schweikard |
| 6,173,715 B1 | 1/2001 | Sinanan |
| 6,198,963 B1 | 3/2001 | Haim et al. |
| 6,239,724 B1 | 5/2001 | Doron et al. |
| 6,363,940 B1 | 4/2002 | Krag |
| 6,363,982 B1 | 4/2002 | Nixon, Jr. |
| 6,371,379 B1 | 4/2002 | Dames |
| 6,385,482 B1 | 5/2002 | Boksberger |
| 6,400,338 B1 | 6/2002 | Mejia |
| 6,401,722 B1 | 6/2002 | Krag |
| 6,441,741 B1 | 8/2002 | Yoakum |
| 6,474,341 B1 | 11/2002 | Hunter |
| 6,518,884 B1 | 2/2003 | Tanji |
| 6,675,810 B2 | 1/2004 | Krag |
| 6,698,433 B2 | 3/2004 | Krag |
| 6,734,795 B2 | 5/2004 | Price |
| 6,812,842 B2 | 11/2004 | Dimmer |
| 6,822,570 B2 | 11/2004 | Dimmer |
| 6,838,990 B2 | 1/2005 | Dimmer |

| | | | |
|---|---|---|---|
| 2001/0018594 A1 | 8/2001 | Krag | |
| 2002/0193685 A1 | 12/2002 | Mate | |
| 2003/0052785 A1 | 3/2003 | Gisselberg | |
| 2003/0088178 A1 | 5/2003 | Owens et al. | |
| 2003/0192557 A1 | 10/2003 | Krag | |
| 2004/0074974 A1 | 4/2004 | Senba | |
| 2004/0127787 A1 | 7/2004 | Dimmer | |
| 2004/0138554 A1 | 7/2004 | Dimmer | |
| 2004/0138555 A1 | 7/2004 | Krag | |

FOREIGN PATENT DOCUMENTS

| | | |
|---|---|---|
| EP | 1034738 | 9/2000 |
| FR | 26335259 | 2/1990 |
| WO | WO-88/08282 | 11/1988 |
| WO | WO-95/33519 | 12/1995 |
| WO | WO-96/08208 | 3/1996 |
| WO | WO-96/08999 | 3/1996 |
| WO | WO-97/36192 | 10/1997 |
| WO | WO-97/48438 | 12/1997 |
| WO | WO-98/30166 | 7/1998 |
| WO | WO-98/58065 | 7/1998 |
| WO | WO-99/13775 | 3/1999 |
| WO | WO-99/17133 | 4/1999 |
| WO | WO-99/27839 | 6/1999 |
| WO | WO-99/30182 | 6/1999 |
| WO | WO-99/35966 | 7/1999 |
| WO | WO-99/44506 | 9/1999 |
| WO | WO-99/58055 | 11/1999 |
| WO | WO-99/58065 | 11/1999 |
| WO | WO-00/12009 | 3/2000 |
| WO | WO-00/24332 | 5/2000 |
| WO | WO-00/51514 | 9/2000 |
| WO | WO-00/71047 | 11/2000 |
| WO | WO-01/34049 | 5/2001 |
| WO | WO-01/54765 | 8/2001 |
| WO | WO-02/19908 | 3/2002 |
| WO | WO-02/100485 | 12/2002 |

OTHER PUBLICATIONS

U.S. Appl. No. 10/416,827, filed Nov. 17, 2000, David Krag.
U.S. Appl. No. 10/746,888, filed Dec. 24, 2003, Margo Gisselberg.
U.S. Appl. No. 10/791,662, filed Mar. 2, 2004, David Krag.
Kelley, William E., MD, Image-Guided Breast Biopsy: The ABBI System, 1997, www.ussurg.com/health-care/procedures/abbi.
International Search Report dated Jan. 24, 2003, PCT Application No. PCT/US02/29390.
International Search Report dated Jul. 3, 2001, PCT Application No. PCT/US00/31667.
International Search Report dated Jan. 24, 2003, PCT Application No. PCT/US02/29390.
Hsiao, K., "Fast Multi-Axis Tracking of Magnetically-Resonant Passive Tags: Methods and Applications," Feb. 2001, Massachusetts Institute of Technology, Dept. of Electrical Engineering and Computer Science.
PCT Written Opinion dated Jul. 8, 2003, PCT Application No. PCT/US00/31667.
International Search Report dated Oct. 8, 2002, PCT Application No. PCT/US02/17876.
The World's Most Versatile Biopsy System Offered Only by USSC, ABBI System Features, © 1997, United States Surgical Corporation, www.ussurg.com/health-care/procedures/abbi.
International Search Report dated Apr. 13, 2001, PCT Application No. PCT/US00/31673.

IMPLANTABLE MARKER WITH A LEADLESS SIGNAL TRANSMITTER COMPATIBLE FOR USE IN MAGNETIC RESONANCE DEVICES

CROSS-REFERENCE TO RELATED APPLICATION(S)

This application is a continuation of U.S. application Ser. No. 10/334,698 filed Dec. 30, 2002 now U.S. Pat. No. 7,289,839, entitled IMPLANTABLE MARKER WITH A LEADLESS SIGNAL TRANSMITTER COMPATIBLE FOR USE IN MAGNETIC RESONANCE DEVICES, which is hereby incorporated by reference.

TECHNICAL FIELD

The present invention is directed toward permanently implantable or semi-permanently implantable markers with wireless signal transmitters that are compatible for use in magnetic resonance devices.

BACKGROUND

Medical procedures often require locating and treating target areas within a patient. Radiation therapy and many surgical procedures require locating the target with a high degree of precision to limit collateral damage to healthy tissue around the target. It is particularly important to know or estimate the precise location of the target in radiation oncology because it is desirable to limit the exposure of adjacent body parts to the radiation. In applications for treating prostate cancer, for example, the colon, bladder or other body part of the patient adjacent to the prostate is desirably not impinged by the high-intensity radiation beam. Surgical applications, such as breast surgery and other procedures involving soft tissue, also require knowing the precise location of a target because a lesion is not necessarily fixed relative to external landmarks on the patient.

Many imaging systems have been used to locate areas or particular targets within a body before performing radiation oncology or surgical procedures. Although x-ray, Magnetic Resonance Imaging (MRI), CT, and other imaging techniques are useful to locate targets within the body at the pre-operative stage of a procedure, they are often not suitable or difficult to use in real time during surgery or radiation therapy. For example, the location of a lesion in soft tissue or an organ within the patient's body may shift relative to external landmarks on the patient between the pre-operative imaging procedure and the actual radiation or surgical procedure. Additionally, when imaging systems are used during a radiation or surgical procedure, they may not provide sufficiently accurate measurements of the location of the lesions and they may interfere with the radiation or surgical procedure. Therefore, imaging techniques by themselves are not suitable for accurately identifying the actual location of a target for many medical applications.

Another technique to locate a target in a patient is to implant a marker relative to the target. For example, implantable markers that generate a signal have been proposed for use to locate a selected target in a patient in radiation oncology procedures. U.S. Pat. No. 6,385,482 B1 issued to Boksberger et al. discloses a device having an implanted emitter unit SE located inside or as close as possible to a target object T and a plurality of receiver units S11, S12, S21 and S22 that are located outside of the patient. Boksberger discloses determining the location of the target object T by energizing the emitter unit SE using generator GE and sensing the signal from the emitter unit SE with the receiver units S11-S22. Boksberger discloses and claims that the receiver units S11-S22 are configured to determine the gradient of the magnetic field generated by the emitter unit SE. Boksberger discloses emitter units SE that are energized using a wired connection to the external generator GE. Boksberger also indicates that it is conceivable to use an emitter unit SE that is energized by a battery or excited by an electromagnetic field generated by the external generator GE. The wired device disclosed in Boksberger, however, may not be suitable for use in radiation oncology and many surgical procedures because it is impractical to leave a wired marker implanted in a patient for the period of time of such procedures (e.g., five to forty days). Moreover, Boksberger does not disclose or suggest anything with respect to providing an implantable emitter unit SE that is compatible for use in magnetic resonance imaging devices after being implanted in a patient.

Another technique to locate a target in a patient is to implant passive, gold fiducials in or near the target site. The positions of the gold fiducials are determined periodically using radiation. Although gold fiducials are useful for localizing a target within a patient, these systems do not provide sufficiently accurate real time measurements of the target site location during radiation oncology procedures.

Other types of tags or markers with resonating magnetic circuits have been developed. These markers have been used to tag sponges and other items used during surgery or locate the general location of feeding tubes or other instruments in other procedures. One significant challenge of miniature, wireless markers is to provide a sufficiently strong signal to be accurately detected by sensors outside of the body.

DETAILED DESCRIPTION

The following disclosure describes several embodiments of wirelessly energized markers configured to be implanted in or externally attached to patients for a long period of time and compatible for use in powerful magnetic fields generated by magnetic resonance imaging devices. Several embodiments and features of markers in accordance with the invention are set forth and described in FIGS. 1-6. It will be appreciated that other embodiments of markers in accordance with the invention can include additional or different features than those shown in FIGS. 1-6. Additionally, it will be appreciated that several embodiments of markers in accordance with the invention do not include all of the features shown in these figures. Additionally, for purposes of brevity, like reference numbers refer to similar or identical components.

Figure 1:
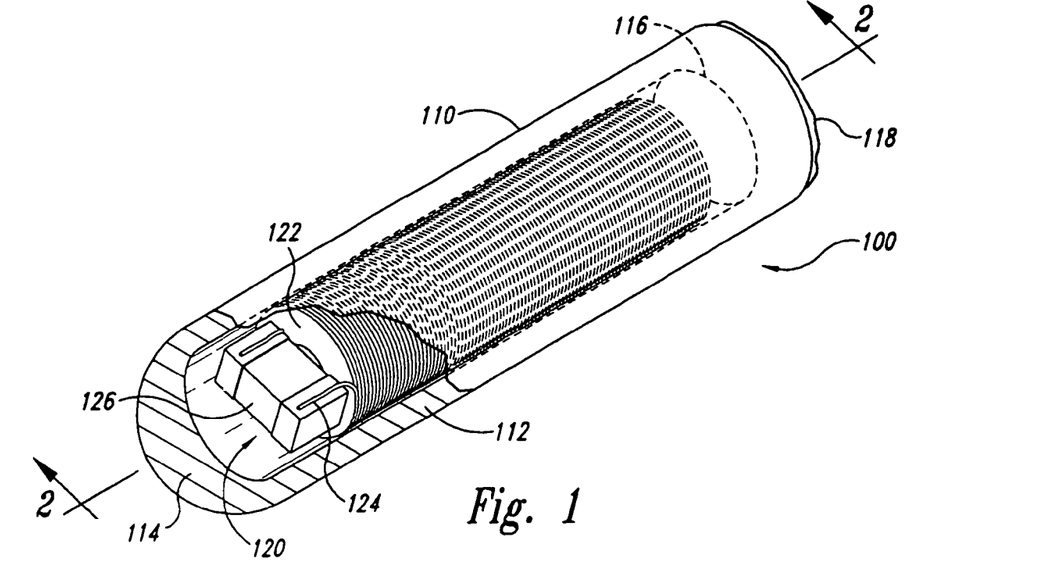
FIG. 1 is an isometric view of an implantable wireless marker in accordance with an embodiment of the invention with a section cut away to illustrate internal components.

FIG. 1 is an isometric view of an implantable marker 100 in accordance with an embodiment of the invention with a portion cut away to illustrate internal components. The embodiment of the marker 100 shown in FIG. 1 includes a casing 110 and a resonating circuit 120 in the casing 110. The casing 110 is a biocompatible barrier configured to be implanted in the patient or otherwise attached to the patient. The casing 110 can be a generally cylindrical capsule that is sized to fit within a 14 gauge needle for percutaneous implantation, but the casing can have other configurations and be larger or smaller. The casing 110, for example, can have barbs to anchor the casing 110 in soft tissue or an adhesive for attaching the casing 110 externally to the skin of a patient. In one embodiment, the casing 110 includes (a) a glass capsule or shell 112 having a closed end 114 and an open end 116, and (b) a sealant 118 in the open end 116 of the shell 112. The casing 110 and sealant 118 can be made from plastics, ceramics, glass or other suitable biocompatible materials.

The resonating circuit 120 produces a wirelessly transmitted signal in response to a wirelessly transmitted excitation signal. In one embodiment, the resonating circuit 120 comprises a coil 122 defined by a plurality of windings of a conductor 124. Many embodiments of the resonating circuit 120 also include a capacitor 126 coupled to the coil 122. The coil 122 resonates at a selected resonant frequency. The coil 122 can resonate at the selected resonant frequency solely using the parasitic capacitance of the windings without having a capacitor, or the selected resonant frequency can be produced using the combination of the coil 122 and the capacitor 126. The coil 122 by itself or in combination with the capacitor 126 accordingly defines a signal transmitter that generates an alternating magnetic field at the selected resonant frequency in response to the excitation signal. The conductor 124 of the illustrated embodiment can be hot air or alcohol bonded wire having a gauge of approximately 45-52 gauge. The coil 122 can have 800-2000 turns. The windings are preferably wound in a tightly layered coil.

The resonating circuit 120 is powered by a wirelessly transmitted excitation signal such that the resonating circuit is leadless, i.e., not connected to external lead wires which extend through or project from the casing 110. In one embodiment, the resonating circuit 120 can be energized by an alternating excitation magnetic field generated externally with respect to the patient at the resonant frequency of the resonating circuit. In response to the excitation field, the resonating circuit 120 produces a marker signal or response signal that can be measured by a sensor array positioned externally with respect to the patient. Suitable devices for generating the magnetic excitation field and sensing the marker signal are disclosed in U.S. patent application Ser. No. 10/027,675 filed on Dec. 20, 2001; Ser. No. 10/044,056 filed on Jan. 11, 2002; and Ser. No. 10/213,980 filed on Aug. 7, 2002, which are herein incorporated by reference.

Figure 2:
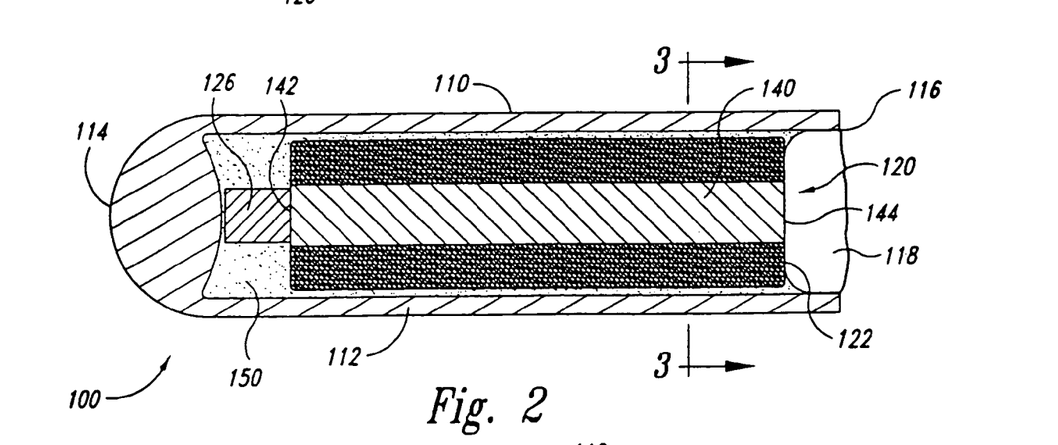
FIG. 2 is a cross-sectional view taken along a longitudinal axis of an embodiment of the marker of FIG. 1.

FIG. 2 is a cross-sectional view of an embodiment of the marker 100 taken along a longitudinal axis 2-2 shown in FIG. 1. The marker 100 further includes a ferromagnetic element 140 having a first end 142 and a second end 144. The ferromagnetic element 140 is at least partially surrounded by the coil 122. In the particular embodiment shown in FIG. 2, the coil 122 surrounds the ferromagnetic element 140 from the first end 142 to the second end 144. In other embodiments, the coil 122 surrounds only a portion of the ferromagnetic element 140. The capacitor 126 can be positioned at the first end 142 of the ferromagnetic element 140. Additionally, the resonating circuit 120 and the ferromagnetic element 140 can be fixed to the casing 110 by an adhesive 150.

The ferromagnetic element 140 is preferably composed of ferrite or other materials that have high magnetic permeability compared to free space. The amount of energy that the inductor is capable of storing is limited, in part, by the magnetic field saturation of the ferromagnetic element 140. To store more energy in a miniature wireless marker, the prior art taught that the size of the ferromagnetic material should be maximized within the limited space of the marker. As shown in FIG. 2, however, the volume of the ferromagnetic element 140 is significantly less than the available volume within the casing 110. The smaller volume of the ferromagnetic element 140 reduces the force exerted on the marker 100 when the marker 100 is placed in a magnetic resonance imaging device having a magnetic field strength of 1.5 T with a corresponding gradient, field of approximately 3 T/m. In one embodiment, the ferromagnetic element has a volume such that when the marker is in a magnetic resonance device, then the force exerted on the marker by the magnetic field is less than gravitational force exerted on the marker. Additionally, the small volume of the ferromagnetic element 140 reduces the size of the artifact in an image from a magnetic resonance device. It will be appreciated that ferromagnetic materials will produce an artifact (i.e., a region in which image information is suppressed) in an image produced by a magnetic resonance imaging device. The volume of the ferromagnetic element 140 can be reduced to a size such that it produces a small artifact in an image from a magnetic resonance device. In general, such ferromagnetic elements 140 have small diameters less than the size of commercially available ferrite rods for transponder applications, which are as small as 0.75 mm in diameter (i.e., ferrite rods available from Ferroxcube of Spain).

Figure 3:
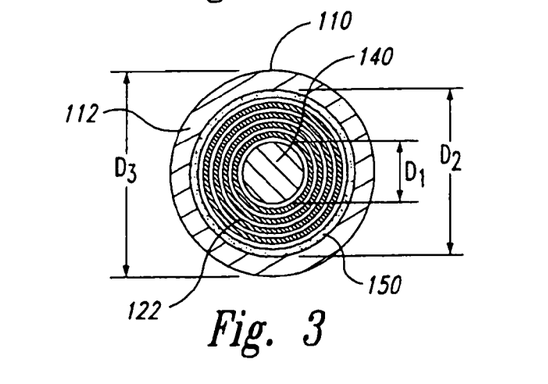
FIG. 3 is a cross-sectional view in a plane normal to a longitudinal axis of a marker in accordance with an embodiment of the marker shown in FIG. 1.

FIG. 3 is a cross-sectional view of the marker 100 taken along line 3-3 of FIG. 2. In one embodiment, the ferromagnetic element 140 is a ferrite rod having a diameter $D_1$ of approximately 0.20-0.70 mm, but the ferromagnetic element 140 can have other cross-sectional configurations in other embodiments. For example, an extruded ferrite rod can have an elliptical, oval or polygonal cross section. The ferromagnetic element 140 can have a length of approximately 2.0-20 mm. In one particular embodiment the ferromagnetic element 140 has a diameter of approximately 0.25-0.50 mm and a length of 2-12 mm, and in another embodiment the ferromagnetic element 140 has a diameter of 0.30-0.35 mm and a length of 4.0-6.0 mm. The coil 122 has an inner diameter of approximately 0.20-0.80 mm and an outer diameter $D_2$ of approximately 0.6-1.4 mm or 0.8-1.9 mm. The casing 110 can have an outer diameter $D_3$ of approximately 1.0-3.0 mm. In other embodiments, the coil 122 can have different inner and outer diameters, and the casing 110 can have a different outer diameter. In another particular embodiment, the diameter $D_1$ of the ferromagnetic element 140 is approximately 0.30-0.50 mm, the inner diameter of the coil 122 is approximately 0.30-0.60 mm, the outer diameter $D_2$ of the coil 122 is approximately 1.2-1.9 mm (or 1.2-1.4 mm), and the outer diameter $D_3$ of the casing 110 is approximately 1.8-2.0 mm. The volume of the ferromagnetic element 140 can be approximately 0.5-19.0 mm$^3$.

The marker 100 is constructed by manufacturing the ferromagnetic element 140, placing the coil 122 around the ferromagnetic element 140, and encapsulating the resonating circuit 120 and the ferromagnetic element 140 in the casing 110. The ferromagnetic element 140 can be manufactured using extrusion, coring, or high pressure molding processes to form a ferrite rod having a diameter of approximately 0.2-0.7 mm. The coil 122 is formed by winding the conductor 124 around either the ferromagnetic element 140, a sleeve around the ferromagnetic element 140, or a mandrel separate from the ferromagnetic element 140. In one embodiment, the conductor 124 is wrapped directly onto the ferromagnetic element 140, but this may not be feasible in many applications because it may break ferromagnetic elements having a diameter less than 0.5 mm. In another embodiment, a retractable sleeve can slide along the ferromagnetic element 140 as the conductor 124 is wound directly onto the ferromagnetic element. The sleeve is expected to support the ferromagnetic element 140 as the first layer of turns are wrapped around the ferromagnetic element 140. The first layer of turns supports the rod so that subsequent layers of turns can be wound onto the first layer. In still another embodiment, the coil 122 is wound around a mandrel separately from the ferromagnetic element 140. The coil 122 is then removed from the mandrel and the ferromagnetic element 140 is inserted into the inner diameter of the coil 122. This embodiment can result in a small gap between the ferromagnetic element 140 and the inner diameter of the coil 122. This gap should be minimized in optimal circumstances to increase the performance of the resonating circuit 120. After the ferromagnetic element 140 is positioned within the coil 122, this assembly is adhered to the casing 110 using the adhesive 150, and the sealant 118 is used to close the open end 116 of the casing 110.

Figure 4:
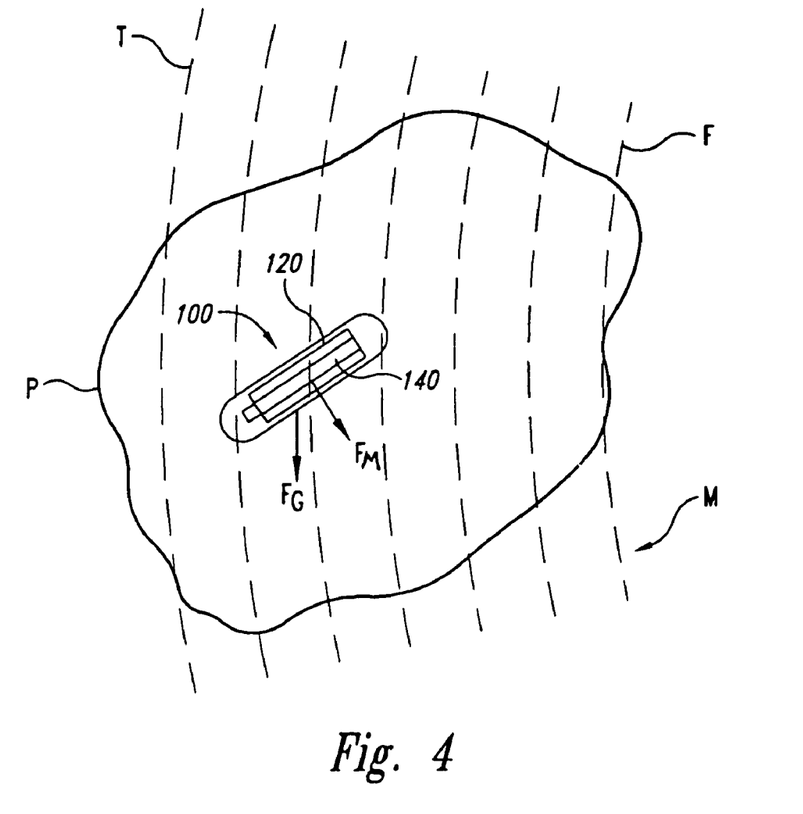
FIG. 4 is a cross-sectional view taken along a longitudinal axis of a marker in accordance with an embodiment of the invention after being implanted in a patient.

FIG. 4 is a representative view of the operation of the marker 100 in an magnetic field M generated by a magnetic resonance imaging device (not shown). The magnetic field M is an imaging magnetic field. In this embodiment, a patient is placed in a magnetic resonance imaging device to image a portion P of the patient. The imaging magnetic field M includes a plurality of flux lines F. Because the ferromagnetic element 140 has a high magnetic permeability, the ferromagnetic element 140 exerts a magnetic force FM in the presence of the magnetic field M due to the presence of DC and gradient magnetic fields. The magnitude of the magnetic force FM is a function of the volume and the type of material (i.e. magnetic saturation) of the ferromagnetic element 140. The volume of the ferromagnetic element 140 is selected so that the magnetic force FM caused by the interaction between the ferromagnetic element 140 and the magnetic field M is less than the gravitational force FG exerted against the marker 100. This will ensure that the magnetic field M does not cause the marker 100 to move within the portion P of the patient any more than the force of gravity will cause movement of the marker 100.

Figure 5:
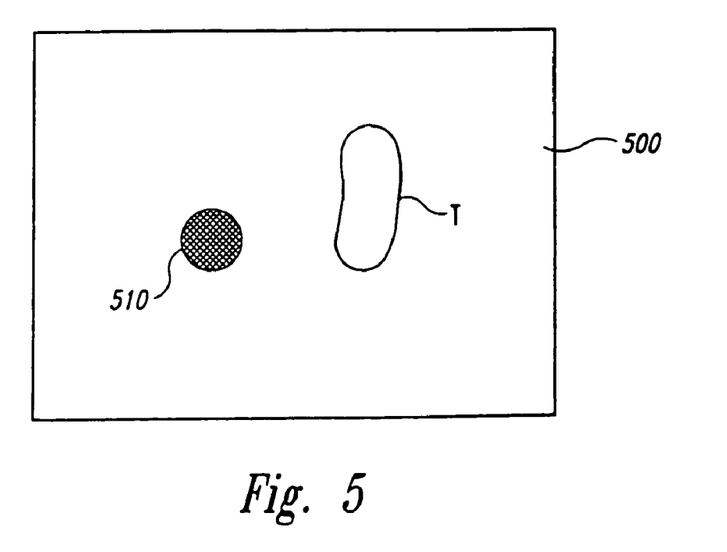
FIG. 5 is a diagram of a display of a magnetic resonance image with an artifact by a magnetic marker.

FIG. 5 is a schematic representation of a magnetic resonance image 500 that shows a target location T within a body part of a patient. The image 500 includes an artifact 510 caused by the ferromagnetic element 140 of the marker 100. The artifact 510 is typically much larger than the size of the marker, and thus it tends to obscure the actual location of the marker and the images of tissue adjacent to the marker. The size of the artifact 510 is related to the size of the ferromagnetic element 140 in the marker 100. In several embodiments, the volume of the ferromagnetic element 140 is selected to produce an artifact not greater than 1,500 mm$^2$ in an image produced by a resonance imaging device field having a DC field strength of 1.5 T. In other embodiments, the volume of the ferromagnetic element 140 is selected to produce an artifact not greater than 400-1,200 mm$^2$, and in other cases not greater than 400-800 mm$^2$ in an image produced by a magnetic resonance imaging device field having a DC field strength of 1.5 T.

Figure 6:
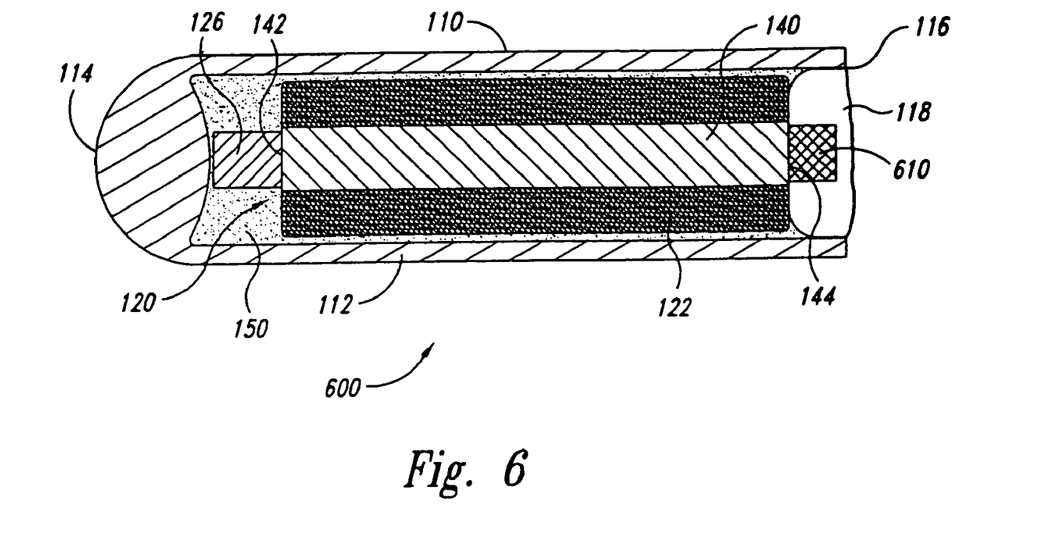
FIG. 6 is a cross-sectional view taken along a longitudinal axis of a marker in accordance with another embodiment of the invention.

FIG. 6 is a cross-sectional view of a marker 600 in accordance with another embodiment of the invention. The marker 600 is substantially similar to the marker 100 shown in FIG. 2, but the marker 600 further includes a module 610 at the second end 144 of the ferromagnetic element 140. The module 610 is preferably configured to be symmetrical with respect to the capacitor 126 at the first end 142 of the ferromagnetic element 140. The module 610, more specifically, is configured to produce a similar radiographic image as the capacitor 126 in an x-ray. In one embodiment, the module 610 is configured such that the magnetic centroid of the marker is at least substantially coincident with the radiographic centroid of the marker. In other embodiments that use CT or other types of imaging modalities, the module 610 is configured to produce a symmetrical image relative to the capacitor 126. For example, the module 610, can be another capacitor identical to the capacitor 126 that may or may not be electrically coupled to the coil 122. In other embodiments, the module 610 can be an electrically inactive element that is not electrically connected to the resonating circuit 120 or another type of electrically active element that is electrically coupled to the resonating circuit 120. Suitable electrically inactive modules include ceramic blocks shaped like the capacitor 126. In either case, one purpose of the module 610 is to have the same characteristics as the electrically active capacitor 126 in x-ray, CT, and other imaging techniques. Since the markers may be located via radiographic methods (e.g. CT, or x-ray) to determine the marker centroid positions relative the target tissue prior to therapy, an error in the position of the marker radiographic and magnetic centroids may result in a fixed positional error during therapy.

From the foregoing, it will be appreciated that although embodiments have been described for purposes of illustration, various modifications may be made without deviating from the spirit and scope of the invention. Accordingly, the invention is not limited except by the appended claims.

I/We claim:

1. A marker for localizing a target within a patient, comprising:
a ferromagnetic element and a plurality of windings around the ferromagnetic element for producing a magnetic field having a magnetic centroid; and
a casing around the ferromagnetic element and the windings, the casing being configured to be positioned relative to a target of the patient, and an element including a radiographic element of the marker having a radiographic centroid within the casing and substantially coincident with the magnetic centroid.

2. The marker of claim 1 wherein the ferromagnetic element and the windings define the magnetic centroid.

3. The marker of claim 1 wherein the radiographic element further comprises a capacitor electrically connected to the windings.

4. The marker of claim 1 further comprising:
the radiographic element having a capacitor electrically connected to the windings; and
the element further including a module having similar radiographic characteristics as the capacitor in a radiographic image.

5. The marker of claim 4 wherein the capacitor is located at one end of the ferromagnetic element and the module is located at another end of the ferromagnetic element.

6. The marker of claim 5 wherein the capacitor and the module have the same characteristics in X-ray images.

7. The marker of claim 5 wherein the capacitor and the module have the same characteristics in CT images.

8. The marker of claim 5 wherein the capacitor and the module are symmetrical relative the radiographic centroid.

9. The marker of claim 5 wherein the ferromagnetic element comprises a ferrite rod having a diameter of approximately 0.2 mm-0.5 mm and a length of approximately 2 mm-12 mm.

10. A marker for localizing a target within a patient, comprising:
   a ferromagnetic element;
   a plurality of windings around the ferromagnetic element for producing a resonating magnetic field having a magnetic centroid; and
   an element at a location relative to the ferromagnetic element, wherein the element is arranged so that a radiographic element of the marker has a radiographic centroid substantially coincident with the magnetic centroid.

11. The marker of claim 10 further comprising the radiographic element having a capacitor electrically connected to the windings, wherein the element comprises a module having similar radiographic characteristics as the capacitor.

12. The marker of claim 10 further comprising the radiographic element having a capacitor electrically connected to the windings and located at one end of the ferromagnetic element, and the element comprises a module having similar radiographic characteristics as the capacitor and located at another end of the ferromagnetic element.

13. The marker of claim 12 wherein the capacitor and the module are symmetrical relative to the radiographic centroid.

14. The marker of claim 10 wherein:
   the ferromagnetic element comprises a ferrite rod having a diameter not greater than approximately 0.7 mm; and
   the marker further comprises a casing around the ferromagnetic element and the windings that has an outer diameter not greater than approximately 2 mm.

15. The marker of claim 10 wherein the ferromagnetic element comprises a ferrite rod having a diameter of approximately 0.2 mm-0.5 mm and a length of approximately 2 mm-12 mm.

16. The marker of claim 10 wherein the ferromagnetic element comprises a ferrite rod having a volume of approximately 0.5 mm$^3$-19.0 mm$^3$.

17. The marker of claim 10 wherein the ferromagnetic element comprises a ferrite rod, and the volume of the rod is less than a volume of ferrite that produces an artifact of 1500 mm$^2$ in an image produced by a resonating magnetic field of approximately 1.5 T.

18. The marker of claim 10 wherein the ferromagnetic element comprises a ferrite rod, and the volume of the rod is less than a volume of ferrite that produces an artifact of 400 mm$^2$-1200 mm$^2$ in an image produced by a resonating magnetic field of approximately 1.5 T.

19. The marker of claim 10 wherein (a) the ferromagnetic element comprises a ferrite rod having a diameter of approximately 0.2 mm-0.6 mm, (b) the windings comprise a coil having an inner diameter of approximately 0.2 mm-0.8 mm and an outer diameter of approximately 1.2 mm-1.9 mm, and (c) the marker further comprises a casing around the ferromagnetic element and the windings that has an outer diameter of approximately 1.5 mm-2.5 mm.

20. The marker of claim 10 wherein;
   the ferromagnetic element comprises a ferrite rod having a diameter of approximately 0.3 mm-0.5 mm;
   the windings comprise a coil having an inner diameter of approximately 0.3 mm-0.6 mm and an outer diameter of approximately 1.2 mm-1.9 mm; and
   the marker further comprises a casing around the ferromagnetic element and the windings that has an outer diameter of approximately 2 mm.

21. A marker for localizing the position of a target within a patient, comprising:
   a ferromagnetic element, wherein the ferromagnetic element has a volume such that when the marker is in an imaging magnetic field having a strength of 1.5 T and a gradient of 3 T/m, then the force exerted on the marker by the imaging magnetic field is not greater than gravitational force exerted on the marker;
   a plurality of windings around the ferromagnetic element for producing a resonating magnetic field having a magnetic centroid; and
   a casing around the ferromagnetic element and the windings, the casing being configured to be positioned relative to a target of the patient, and an element including a radiographic element of the marker having a radiographic centroid within the casing and substantially coincident with the magnetic centroid.

22. The marker of claim 21 wherein the ferromagnetic element and the windings define the radiographic centroid.

23. The marker of claim 21 further comprising the radiographic element having a capacitor electrically connected to the windings.

24. The marker of claim 21 further comprising:
   the radiographic element having a capacitor electrically connected to the windings; and
   the element including a module having similar radiographic characteristics as the capacitor in a radiographic image.

25. The marker of claim 24 wherein the capacitor is located at one end of the ferromagnetic element and the module is located at another end of the ferromagnetic element.

26. The marker of claim 25 wherein the capacitor and the module have the same characteristics in X-ray images.

27. The marker of claim 25 wherein the capacitor and the module have the same characteristics in CT images.

28. The marker of claim 25 wherein the capacitor and the module are symmetrical relative to the radiographic centroid.

29. A method of localizing a target of a patient, comprising:
   imaging a radiographic element of a marker implanted in the patient using a radiographic imaging modality, the marker having an element at a location relative to a ferromagnetic core, the ferromagnetic core has a plurality of windings around the core capable of producing a resonating magnetic field having a magnetic centroid, and wherein the element is arranged so that the radiographic element of the marker further has a radiographic centroid configured to be within a casing and substantially coincident with the magnetic centroid;
   generating a magnetic excitation field that causes the marker to produce the resonating magnetic field; and
   sensing the resonating magnetic field to locate the marker.

* * * * *

UNITED STATES PATENT AND TRADEMARK OFFICE
CERTIFICATE OF CORRECTION

PATENT NO. : 7,778,687 B2  Page 1 of 1
APPLICATION NO. : 10/745097
DATED : August 17, 2010
INVENTOR(S) : Steven C. Dimmer et al.

It is certified that error appears in the above-identified patent and that said Letters Patent is hereby corrected as shown below:

On page 2, in column 2, under "U.S. Patent Documents", line 72, delete "Dimmer" and insert -- Dimmer et al. --, therefor.

On page 3, in column 2, under "Other Publications", line 4, delete "ABBI" and insert -- ABBI* --, therefor.

On page 3, in column 2, under "Other Publications", line 21, delete "ABBI" and insert -- ABBI* --, therefor.

In column 4, line 17, delete "gradient," and insert -- gradient --, therefor.

In column 6, line 14, delete "610," and insert -- 610 --, therefor.

Signed and Sealed this

Seventh Day of December, 2010

David J. Kappos
*Director of the United States Patent and Trademark Office*